United States Patent [19]

Schrage

[11] 4,107,169

[45] Aug. 15, 1978

[54] METHOD OF PREPARING 2-ARYL BENZOXAZOLES AND 2-ARYL BENZOTHIAZOLES

[75] Inventor: Klaus Schrage, Konigswinter, Fed. Rep. of Germany

[73] Assignee: Dynamit Nobel Aktiengesellschaft, Troisdorf, Fed. Rep. of Germany

[21] Appl. No.: 789,301

[22] Filed: Apr. 20, 1977

[30] Foreign Application Priority Data

May 4, 1976 [DE] Fed. Rep. of Germany ....... 2619547

[51] Int. Cl.$^2$ .......................................... C07D 277/66
[52] U.S. Cl. ........................... 260/304 P; 260/307 D; 260/296 H
[58] Field of Search ............ 260/304 P, 307 D, 296 H

[56] References Cited

U.S. PATENT DOCUMENTS 2,985,661   5/1961   Hein et al. ....................... 260/304 P

*Primary Examiner*—Nicholas S. Rizzo
*Attorney, Agent, or Firm*—Burgess, Dinklage & Sprung

[57] ABSTRACT

A method is provided for the preparation of 2-arylbenzoxazoles and 2-arylbenzthiazoles which comprises reacting a trichloromethyl-substituted aromatic compound with an aromatic compound carrying one amino group and one hydroxy or mercapto group in ortho position to each other. The compounds obtained by the process of the invention form the basis of numerous optical brighteners and find use in dyes, cosmetics, pharmaceuticals and heat-resistant fibers.

9 Claims, No Drawings

METHOD OF PREPARING 2-ARYL BENZOXAZOLES AND 2-ARYL BENZOTHIAZOLES

BACKGROUND

The methods of the prior art for the preparation of 2-aryl benzoxazoles can be reduced to two basic patterns. In both cases, o-aminophenols are starting materials. In the one method, these are reacted with aromatic carboxylic acids or their derivatives, usually acid chlorides, to form o-hydroxybenzanilides, and then these are cyclized in a second step, usually with the aid of catalysts. The other method produces azomethines through reaction with aromatic aldehydes. The cyclization to benzoxazole is then performed by means of an oxidant. The same procedural steps can be applied for the preparation of 2-aryl benzothiazoles, using o-amino thiophenols as starting materials, Benzoxazoles and benzthiazoles are the basis of numerous optical brighteners. Furthermore, compounds having a benzoxazole structure find use in dyes, cosmetics, pharmaceuticals and heat-resistant fibers.

THE INVENTION

The subject of the invention is a method of preparing 2-arylbenzoxazoles and 2-arylbenzothiazoles, which is characterized by the reaction of trichloromethyl aromatics compounds with aromatic compounds carrying one amino group and one hydroxy or mercapto group in the ortho position with respect to one another.

Benzoxaxoles and benzthiazoles in the meaning of the invention are to be considered those oxazoles and thiazoles which carry a mononuclear or polynuclear, carbocyclic or heterocyclic, aromatic ring condensed to the oxazole or thiazole ring.

The reaction can be represented diagrammatically by the following equation:

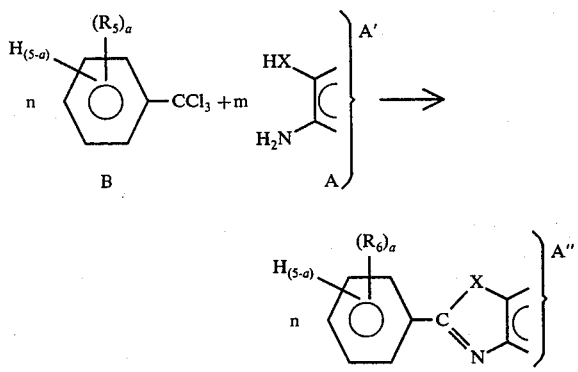

In this equation, $R_5$ represents substituents remaining unaltered in the reaction on the aromatic nucleus of the trichloromethyl aromatic compound, or the groups —$CCl_3$ or COCl; $a$ represents the number of substituents $R_5$, and is an integer from 0 to 5; A' represents the integrating moiety of a mononuclear or polynuclear aromatic compound, such as, for example, in the case of substituted or unsubstituted 2-aminophenols or 2-aminothiophenols, as the case may be, the group:

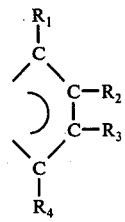

wherein, for example in the case of the o-aminohydroxy pyridines, one of the carbon atoms and its substituent is replaced by N, or in the case of the naphthalene derivatives, two of the substituents $R_1$, $R_2$, $R_3$ or $R_4$ on adjacent carbon atoms are replaced by the group

or, in the case of quinolines, two like adjacent substituents on the pyridine nucleus are replaced by the group

which can also carry one or more of the substituents $R_1$ to $R_4$; HX— represents the moieties HO— or HS, and $n$ and $m$ represent the molar amounts of the reactants B or A participating in the reaction, and amounting to 1 or 2.

The $R_5$ substituents of B which remain unaltered during the reaction are not restricted as to kind. Possible substituents of this kind are especially single-bond substituents from the group: halogen, especially Cl— or also Br—, carboxyl or carboxylic acid alkyl esters having 1 to 6 carbon atoms in the alkyl group, or in some cases also alkyl moieties of 1 to 6 carbon atoms, the group $O_2N$— and others.

If $R_5$ represents either of the groups —$CCl_3$ or —COCl participating in the formation of benzoxazole or benzothiazole rings, it is preferable that only one more of these groups be present.

Preferred are one or two of these substituents $R_5$ or H as substituent.

In the formula shown for reactant B, the $R_5$ substituents can also be the groups HX— $H_2N$—, but to have one group HX and one group $H_2N$— in the ortho position to one another is undesirable if one wishes to avoid the formation of mixtures of reaction products. Preferrably in reactant B no HX— or $H_2N$—group is present.

The substituents $R_1$, $R_2$, $R_3$ and $R_4$ can be any substituent remaining unaltered in the reaction, such as any one of the above-mentioned substituents which remain unaltered in the reaction, or they may be the phenyl moiety, for example. The substituents HX— and $H_2N$— are similarly possible, but having an additional HX group in ortho position to the $H_2N$— group that is present is not preferred, nor is having an additional $H_2N$ group in ortho position to the HX— group, where one wishes to avoid the formation of mixtures of products. Preferrably in reactant A one group HX— and one group $H_2N$— is present.

It is possible, however, where the formation of the bis-oxazoles and bis-thiazoles is desired, the presence of two additional substituents $R_2$ and $R_3$, having the meaning $H_2N-$ and $HX-$ in ortho position to one another.

The groups $-CCl_3$ and $-COCl$ are not preferred in the integrating moiety $A'$, because then, too, mixtures of reaction products are formed.

The relative molar amounts $n$ and $m$ are accordingly in the ratio of 1 : 1 for the formation of the monooxazoles and monothiazoles, i.e., whenever $R_5$ and $R_1$ to $R_4$ substituents are not ones forming oxazole rings or thiazole rings and remaining unaltered in the reaction. In that case, $R_6 = R_5$ and $A'' = A'$.

The relative molar amount $m : n$ are in the ratio of 2 : 1 for the formation of bisoxazoles and bisthiazoles, in which case one of the substituents $R_5$ has the meaning $-CCl_3$ or $-COCl$, and one of the substituents $R_6$ has the meaning

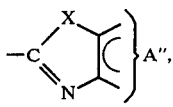

$A''$ being equal to $A'$, and the other substituents $R_6$ being equal in kind and number to $R_5$.

When the relative molar amount $m : n$ is in the ratio of 1 : 2, there is provided the formation of additional bisoxazoles and bisthiazoles, in which case, one of two substituents $R_2$ and $R_3$ on carbon atoms adjacent to one another in group $A'$ will have the meaning $HX-$ and one will have the meaning $H_2N-$, and in the group $A''$ two adjacent substituents on the benzene, pyridine or naphthaline etc. ring will form the grouping.

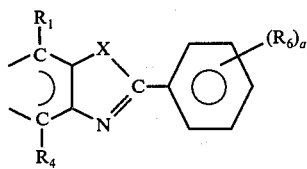

in which $R_6 = R_5$.

Thus far no limitation has been found for this general reaction, so that the examples and formulas stated indicate only what is typical of the reaction without limiting it in any way.

This kind of reaction is surprising since it is known that trichloromethyl aromatic compounds react with phenols as a rule by substitution in the nucleus to form benzophenols.

It is especially advantageous that the process can be performed as a single-step reaction resulting in good yields.

The salts of the 2-aminophenols and 2-aminothiophenols include any acid addition salts, especially their hydrochlorides.

The trichloromethyl aromatic compounds are preferably substituted or unsubstituted trichloromethylbenzenes, although the trichloromethyl derivatives of other aromatic compounds, such as naphthalene, diphenyl and pyridine, can be produced.

The reaction is performed in the temperature range of about 130° to about 250° C, preferably about 180° to about 220° C.

The reaction is performed preferably at normal pressure.

The group $-COCl$ likewise reacts in a single-step reaction, in the presence of catalysts such as $B_2O_3$, at temperatures beginning at about 180° C.

If the reactants are heated after mixing, a runaway reaction sets in beginning at about 130° C, depending on the reactants, accompanied by a severe rise in temperature, which in the case of relatively large batches cannot be brought under control. The reaction is most successful when, in the absence of solvents, and at temperatures between about 165° and about 195° C, the trichloromethyl aromatic compound is added drop by drop, with stirring, to the o-aminophenol or o-aminothiophenol, as the case may be, or better yet their salts. In that case a steady stream of hydrogen chloride will escape and a melt will be obtained which will solidify after cooling to room temperature. However, it is also possible to add the o-aminophenol or o-aminothiophenol to the trichloromethyl aromatic compound.

If catalysts are used, such as $ALCl_3$, $FeCl_3$, $ZnCl_2$, etc., the reaction can be performed smoothly beginning at 130° C.

Solvents or suspension media such as o-dichlorobenzene, decaline or hexachlorobutadiene have shown to advantage over the reaction in substance.

In general, equimolar amounts of the reactants are used. Slight excesses of one or the other component, of up to about 20%, can be used.

The working up of the reaction product can be accomplished by distillation, recrystallization, sublimation or chromatography. The crude yields amount to from 40 to 80%, depending on the procedure and refinement methods.

EXAMPLES

For the sake of simplicity, the 2-aminophenols and 2-aminothiophenols are designated in these examples as A, and benzotrichloride and other trichloromethyl aromatic compounds as B, and the compounds prepared as I to XXII.

EXAMPLE 1 — Preparation of 2-phenylbenzoxazole (I)

(a) 16.4 g (0.15 mol) of 2-aminophenol (A) were heated by a metal bath in a flat-ground flask with a wall-running stirrer, a dropping funnel, a gas introduction tube and a reflux condenser. At a bath temperature of 180° C, 29.3 g (0.15 mol) of benzotrichloride (B) was added drop by drop over a period of 30 minutes. The mixture was let stand for another 2½ hours at room temperature while nitrogen was passed through, and was then cooled and ground with a pestle. 26.4 g was obtained of a brown powder, which was extracted from benzene. The concentrated benzene phase was fed to a small column containing aluminum oxide (Wölm, neutral) and compound I was eluted with benzene: 17.2 g of raw product melting at 99°–101° C (59% of the theory). Upon the recrystallization of a small specimen from etthanol, the melting point increases to 102°–105° C.

$C_{13}H_9NO$ (195.2) Calc. C, 79.97; H, 4.65, O 8.20; N, 7.18. Found: C, 80.0; H, 4.9; O, 8.2; N, 7.1.

(b) If the experiment is performed in the same manner with 21.8 g (0.15 mol) of 2-aminophenol hydrochloride, 22.0 g of raw product is obtained with a melting point of 101° to 103° C (75% of the theory).

(c) 16.4 g (0.15 mol) of 2-aminophenol (A) was refluxed together with 75 ml of decaline in the apparatus described under (a). 29.3 g (0.15 mol) of benzotrichloride (B) was added drop by drop over a period of 15 minutes, and the mixture was heated for another 3 hours with gentle refluxing. Then it was suction filtered while hot and concentrated by evaporation under dry. One half was chromatographed through $Al_2O_3$: 7 g of Compound I, melting point 99°–100° C (41% of the theory). Of the remaining half, one gram was sublimed at 140° C and 0.2 mm Hg; 0.8 g of Compound I, melting point 100°–103° C (44% of the theory).

EXAMPLE 2 — Preparation of 2-phenylbenzothiazole (II)

As in Example 1b, 16.2 g (0.1 mol) of 2-aminothiophenol hydrochloride is reacted at 180° C bath temperature with 19.5 g (0.1 mol) of benzotrichloride (B). By extracting the reaction products with benzene and chromatographing the benzene extract on an $Al_2O_3$ column, 7.0 grams of Compound II were obtained, M.P. 105°–110° C (33% of the theory). A small specimen was recrystallized from ethanol: M.P. 113°–114° C.

$C_{13}H_9NS$ (211.3) calc. C, 73.91; H, 4,29; N, 6.63. Found: C, 73.8; H, 4.0; N, 6.6.

EXAMPLE 3 — Preparation of 2-phenyloxazolo (5,6) pyridine (III)

14.6 g (0.1 mol) of 2-amino-3-hydroxypyridine hydrochloride were reacted with benzotrichloride as in Example 1b. By extraction with benzene and chromatography on an aluminum trioxide column at 75° C, 9 g of Compound III is obtained, M.P. 99°–102° C (46% of the theory). Upon recrystallization from 30 ml of ethanol: M.P. 112° C.

$C_{12}H_8N_2O$ (196.2) calc. C, 73.46; H, 4.11; N, 14.27; Found C, 73.0; H, 4.1; N, 14.2.

EXAMPLES 4 to 11 — Preparation of 2-phenylbenzoxazoles from substituted o-aminophenols (Compounds IV–XI)

The 2-phenylbenzoxazoles listed in table 1 were prepared in the manner described under Example 1 from the specified o-aminophenols or their salts and benzotrichloride (B). The time during which B was added amounts to from one-half to three quarters of an hour, and the post-reaction time to about 3 hours.

The formulas for the substances produced are given in Table 1, and the reaction conditions and the analyses in Tables 2 and 3.

The starting substance of Compound XI is 2-amino-3-hydroxynaphthalene.

Table 1:

| Phenyloxazole | 2-phenylbenzoxazoles Compound | $R_1$ | $R_2$ | $R_3$ | $R_4$ |
|---|---|---|---|---|---|
| | IV | — | $CH_3$ | — | — |
| | V | — | Cl | — | — |
| | VI | — | $NO_2$ | — | — |
| | VII | — | — | $NO_2$ | — |
| | VIII | — | — | Ph | — |
| | IX | — | $NO_2$ | — | Cl |
| | X | — | $COOCH_3$ | — | — |

Table 2

| Compound No. | 2-phenylbenzoxazoles, reaction and finishing operation | | | | | | |
|---|---|---|---|---|---|---|---|
| | Aminophenol used Base (mols) | x HCl (mols) | BTC* (mols) | Extraction in | $Al_2O_3$ chromatography (° C) | g | Raw Product % of the theory |
| IV | — | 0.1 | 0.1 | Benzene | 70 | 14.0 | 67 |
| V | — | 0.1 | 0.1 | " | 70 | 18.0 | 78 |
| VI | — | 0.1 | 0.1 | " | 70 | 14.0 | 58 |
| VII | — | 0.1 | 0.1 | " | 70 | 13.6 | 57 |
| VIII | — | 0.05 | 0.05 | Xylene | 115 | 6.5 | 48 |
| IX | — | 0.1 | 0.1 | " | 120 | 22.9 | 83 |
| X | 0.05 | — | 0.05 | Benzene | 70 | 4.0 | 32 |
| XI | — | 0.1 | 0.1 | Xylene | 110 | 17.8 | 73 |

*Benzotrichloride

Table 3:

| Compound | 2-Phenylbenzoxazoles, Analyses | | | | | Calculated Found | | |
|---|---|---|---|---|---|---|---|---|
| | Recrystallization Solvent | M.P. (° C) | Formula | Analysis C | H | O | N | Cl |
| IV | Petroleum ether | 102–104 | $C_{14}H_{11}NO$ | 80.36 | 5.30 | 7.65 | 6.69 | — |
| | | | | 79.5 | 5.0 | 7.5 | 6.6 | — |
| V | Benzene | 110 | $C_{13}H_8NOCl$ | 67.99 | 3.51 | 6.97 | 6.10 | 15.44 |
| | | | | 67.8 | 3.4 | 6.9 | 5.9 | 15.9 |
| VI | Ethanol | 170–172 | $C_{13}H_8N_2O_3$ | 65.00 | 3.36 | 19.88 | 11.66 | — |
| | | | | 64.7 | 3.3 | 20.2 | 11.7 | — |
| VII | Benzene | 181–183 | $C_{13}H_8N_2O_3$ | 65.00 | 3.36 | 19.88 | 11.66 | — |
| | | | | 64.7 | 3.4 | 19.9 | 11.1 | — |
| VIII | Benzene | 133 | $C_{19}H_{13}NO$ | 84.11 | 4.83 | 5.89 | 5.16 | — |
| | | | | 83.5 | 4.8 | 6.4 | 5.1 | — |
| IX | Benzene | 165–166 | $C_{13}H_7N_2O_3Cl$ | 56.85 | 2.87 | 17.47 | 10.19 | 12.91 |
| | | | | 56.8 | 1.4 | 18.5 | 10.4 | 12.8 |
| X | n-Butanol | 156–157 | $C_{15}H_{11}NO_3$ | 71.14 | 4.38 | 18.95 | 5.53 | — |
| | | | | 71.4 | 4.3 | 18.8 | 5.5 | — |
| XI | Acetone/$H_2O$ | 133–135 | $C_{17}H_{11}NO$ | 83.24 | 4.52 | 6.52 | 5.71 | — |
| | | | | 82.4 | 4.2 | 6.4 | 5.6 | — |

EXAMPLE 12 — Preparation of 2-(4-(Chlorophenyl)-benzoxazole (XII)

In the apparatus described in Example 1a, 14.6 g of 2-aminophenol hydrochloride (0.1 mol) was heated at 180° C and 23.0 g (0.1 mol) of -chlorobenzotrichloride is added drop by drop over a period of ¾ of an hour.

After 3 hours at 190° C, the mixture was cooled and ground with a pestle and extracted thrice with 50 ml of benzene each time. The benzene phases were fed through an aluminum trioxide column, yielding 13.5 g of raw product (59% of the theory) of a melting point of 138°–144° C. A specimen was recrystallized from ethanol, giving a melting point of 149°–150° C.

$C_{13}H_8NOCl$ (229.7) Calc. C, 67.99; H, 3.51; N, 6.10; O, 6.97. Found: C, 67.4; H, 3.4; N, 5.9; O, 6.8;

EXAMPLE 13 — Preparation of 2-(2-chlorophenyl)-benzoxazole (XIII)

In a large test tube with gas introduction and discharge tubes and a glass rod for stirring, 3.7 g of 2-aminophenol hydrochloride (0.025 mole) was heated at 180° C while nitrogen gas was passed through the reactor, and 5.7 g of o-chlorobenzotrichloride (0.025 mol) was added drop by drop over a period of 10 minutes. After 2 hours at 190° C, the mixture was cooled and extracted twice with benzene.

The benzene phases were put through an aluminum trioxide column. The residue after evaporation was recrystallized from 5 ml of isopropanol: 1.2 g of Compound XIII, M.P. 72° C.

$C_{13}H_8NOCl$ (229.7) Calculated: C, 67.99; H, 3.51; N, 6.09; O, 6.97; Cl, 15.44. Found: C, 67.6; H, 3.6; N, 6.3; O, 6.7; Cl, 15.8.

EXAMPLE 14 — Preparation of 2-(4-Chlorophenyl)-5-chlorobenzoxazole (XIV)

Compound XIV was prepared as in Example 12 at 180° C from p-chlorobenzotrichloride and 2-amino-4-chlorophenol hydrochloride, and purified through a preheated aluminum trioxide column: 16 g of raw product, M.P. 178°–183° C (61% of the theory). Upon recrystallization from benzene: M.P. 190°–192° C.

$C_{13}H_7ONCl_2$ (264.1) Calculated: C, 59.12; H, 2.67, O, 6.06; N, 5.30, Cl, 26.85. Found: C, 59.1; H, 2.5; O, 6.3; N, 5.1; Cl, 26.2.

EXAMPLE 15 — Preparation of 2-(4-Chlorophenyl)-5-nitrobenzoxazole (XV)

Compound XV was prepared as in Example 12 at 180°–200° C from p-chlorobenzotrichloride and 2-amino-4-nitrophenol hydrochloride, and purified through a preheated $Al_2O_3$ column: 3.4 g of raw product melting at 205°–210° C (12% of the theory). After recrystallization from benzene: melting point 217°–218° C.

$C_{13}H_7N_2O_3Cl$ (247.6) Calc: C,56.84; H,2.57; N,10.21. Found: C, 56.7; H, 2.5; N, 10.0.

EXAMPLE 16 — Preparation of 2-(4-carbomethoxyphenyl)-benzoxazole (XVI)

In the apparatus described in Example 1, 25.4 g of 4-trichloromethylbenzoic acid methyl ester (0.1 mol) and 10.9 g of 2-aminophenol (0.1 mol) were mixed and slowly heated up to 200° C, so that the stream of HCl that commences at 130° C would not become too strong. The total reaction time was about 4 hours. The ground reaction product was washed thrice with 100 ml of hot benzene and the combined and concentrated benzene phases where chromatographed through an $Al_2O_3$: 8.9 g of raw product XVI, melting point 190°–191° C (35% of the theory), becoming 193°–194° C after recrystallization from benzene.

$C_{15}H_{11}NO_3$ (253.3) Calculated: C, 71.14; H, 4.38; O, 18.95; N, 5.53. Found: C, 71.1; H, 4.4; O, 18.9; N, 5.4.

Example 17 — Preparation of 2-(4-carbomethoxyphenyl)-5-carbomethoxybenzoxazole (XVII)

In the apparatus described in Example 13, under a current of nitrogen gas, 3.3 g 3-amino-4-hydroxybenzoic acid methyl ester (0.02 mol) and 4.8 g trichlormethylbenzoic acid methyl ester (0.02 mol) were mixed and slowly heated to 180°–190° C. Reaction time was 3 hours. The reaction was ground in a mortar and extracted thrice with 80 ml of xylene and passed through an aluminum trioxide column heated at 110° C. 2.3 g of raw product resulted, melting at 195°–210° C (37% of the theory). After recrystallization in p-xylene the melting point was 226°–227° C.

$C_{17}H_{13}NO_5$ (311.3) Calculated: C, 65.59; H, 4.21; O, 25.70; N, 4.50. Found: C, 65.8; H, 4.0; O, 25.6; N, 4.6.

EXAMPLE 18 — Preparation of 2-(4-carbomethoxyphenyl)-5-carboxybenzoxazole (XVIII)

In the apparatus described in Example 1, 12.7 g of 4-trichloromethylbenzoic acid methyl ester (0.05 mol) and 7.5 g of 3-amino-4-hydroxybenzoic acid (0.05 mol) were mixed and heated for 6 hours at 200° C. The reaction product after grinding in a mortar was extracted twice with 100 ml of $CHCl_3$ and then, after drying, twice with 100 ml of water. 9.2 g of raw product remained, melting at 275° to 284° C (62% of the theory). After two recrystallizations with dimethyl formamide plus active charcoal and dimethylsulfoxide, the melting point was 291° to 293° C.

$C_{16}H_{11}NO_5$ (297.3) Calculated: C, 64.65; H, 3.73; O, 26.91; N, 4.71. Found: C, 63.9; H, 3.9; O, 27.3; N, 4.6.

EXAMPLE 19 — Preparation of 2,2'-p-phenylene-bis-benzoxazole (XIX)

In the apparatus described under Example 1, 21.8 g of reactant A (0.2 mol), 25.8 g of p-trichloromethyl-benzoyl chloride (0.1 mol) and 3.5 g of $B_2O_3$ (0.05 mol) were mixed and slowly heated. Between 190° and 200° C, a vigorous evolution of HCl began. After 2 hours the mixture was cooled and ground in a mortar. After extraction twice with 100 ml of $CHCl_3$ and twice with 100 ml of water, 22.3 g of raw product (71% of the theory) was obtained, melting at 318° to 328° C. Compound XIX can be recrystallized from dimethylformamide, o-dichlorobenzene, nitrobenzene, dimethylsulfoxide or 1,2-dibromoethane. A small specimen recrystallized from o-dichlorobenzene melted at 325° to 329° C. The product can be further purified by chromatography on $Al_2O_3$ with 1,2-dibromoethane as the elutant at 120° C, whereupon the melting point becomes 340° to 342° C.

$C_{20}H_{12}N_2O_2$ (312.3) Calc. C, 76.91; H, 3.87; O, 10.25; N, 8.97. Found C, 76.6; H, 3.9; O, 10.7; N, 8.9.

EXAMPLE 20 — Preparation of 2,2'-p-phenylene-6,6'-dinitro-bis-benzoxazole (XX)

In the apparatus described in Example 1, 15.7 g of 1,4-bis-(trichloromethyl)-benzene (0.05 mol) was mixed with 19.1 g of 2-amino-5-nitrophenol hydrochloride (0.1 mol) and slowly heated to 180° C. After 4 hours the mixture was cooled, ground in a mortar and extracted thrice with 50 ml of dibromoethane. The filtrate was passed at 110° C through an $Al_2O_3$ column, yielding 4 g of XX melting at 300°–310° C (20% of the theory). After recrystallization from o-dichlorobenzene: M.P. 315°–317° C.

$C_{20}H_{10}N_4O_6$ (402.3) Calculated: C, 59.71; H, 2.51; N, 13.93; O, 23.86. Found: C, 59.5; H, 2.3; N, 13.4; O, 24.1.

EXAMPLE 21 — Preparation of 2,2'-m-phenylene-6,6'-dinitro-bis-benzoxazole (XXI)

In the same manner as in Example 20, 31.3 g of 1,3-bis-(trichloromethyl)-benzene (0.1 mol) and 38.1 g of 2-amino-5-nitrophenol hydrochloride (0.05 mol) were reacted for 3 hours at 200° C. The product was ground in a mortar and then extracted first thrice with 50 ml of p-xylene and then thrice with 50 ml of dibromoethane. The dibromoethane filtrate was passed at 125° C through an $Al_2O_3$ column, resulting in 25.5 g of XXI (64% of the theory), melting at 258°–260° C. After recrystallization from o-dichlorobenzene: M.P. 275°–277° C.

$C_{20}H_{10}N_4O_6$ (402.3) Calculated: C, 59.71; H, 2.51; N, 13.93; O, 23.86. Found: C, 60.2; H, 2.4; N, 13.5; O, 23.6.

EXAMPLE 22 — Preparation of 2,6-diphenylbenzo-(1,2-d:4,5-d')-bisoxazole (XXII)

In the apparatus described in Example 13, 5.9 g of 2,5-diaminohydroquinone hydrochloride (28 m moles) were placed and at 180° C, 7.6 g of benzotrichloride (39 m moles) were added drop by drop. After 3 hours of heating at 190° C, the mixture was cooled and ground with mortar and pestle. The reaction product was extracted twice with 150 ml of xylene and passed through an aluminum oxide column heated at 125° C. The product was 4.5 g of crude XXII (74% of the theory). After two recrystallizations from xylene the melting point was 319°–323° C.

$C_{20}H_{12}N_2O_2$ (312.2) Calculated: C, 76.91; H, 3.87; O, 10.25; N, 8.97. Found: C, 76.5; H, 4.1; O, 10.4; N, 8.9.

In any of the above working examples, substitution of the corresponding amount of the thiophenol for the analagous phenol reactant shown, will yield the desired benzthiazoles.

What is claimed:

1. A method for preparing a 2-aryl benzoxazoles or 2-aryl benzthiazoles which comprises reacting a trichloromethyl aromatic compound with an aromatic compound carrying one amino group and one hydroxy or mercapto group in the ortho position with respect to the amino group or an acid addition salt thereof at about 130° to about 250° C.

2. A method of claim 1 wherein the o-aminophenol or o-aminothiophenol is in the form of an acid addition salt.

3. A method of claim 2 wherein the acid addition salt is the hydrochloride.

4. A method of claim 1 wherein the reaction is carried out at a temperature of about 180° to about 220° C.

5. A method of claim 2 wherein the reaction is performed at a temperature of about 180° to about 220° C.

6. A method of claim 1 wherein the reaction is performed by adding the trichloromethyl aromatic compound in portions drop by drop to the o-aminophenol or o-aminothiophenol compound or its acid addition salts heated to the reaction temperature.

7. A method of claim 2 wherein the reaction is performed by adding the trichloromethyl aromatic compound drop by drop to the o-aminophenol or o-aminothiophenol compound or its acid addition salts heated to the reaction temperature.

8. A method of claim 6 wherein the reaction temperature is about 180° to about 220° C.

9. A method of claim 7 wherein the reaction temperature is about 180° to about 220° C.

* * * * *

UNITED STATES PATENT AND TRADEMARK OFFICE
CERTIFICATE OF CORRECTION

PATENT NO. : 4,107,169
DATED : August 15, 1978
INVENTOR(S) : Klaus Schrage

It is certified that error appears in the above-identified patent and that said Letters Patent are hereby corrected as shown below:

column 4, line 23, change "to" to --no-- column 5, line 3, change "under" to --until-- column 8, line 2, change "where" to --were-- column 10, line 28, after "portions" insert --or--.

Signed and Sealed this

Third Day of April 1979

[SEAL]

Attest:

RUTH C. MASON
Attesting Officer

DONALD W. BANNER
Commissioner of Patents and Trademarks